United States Patent [19]

Frazier

[11] 4,238,483

[45] Dec. 9, 1980

[54] ANTIMICROBIAL COMPOSITIONS OF MATTER AND A PROCESS FOR PREPARING ANTIMICROBIAL COMPOSITIONS OF MATTER FROM NATURALLY OCCURRING FLAVANOID GLYCOSIDES

[76] Inventor: Stephen E. Frazier, 3521 Pinetree Rd., Orlando, Fla. 32804

[21] Appl. No.: 58,810

[22] Filed: Jul. 19, 1979

[51] Int. Cl.$^3$ .................... A61K 31/70; C07H 15/00; C07H 17/00
[52] U.S. Cl. .......................................... 424/180; 536/8
[58] Field of Search ............................. 424/180; 536/8

[56] References Cited

U.S. PATENT DOCUMENTS

| | | | |
|---|---|---|---|
| 2,534,275 | 12/1950 | Krewson et al. | 536/8 |
| 2,700,047 | 1/1955 | Wilson | 536/8 |
| 2,744,920 | 8/1956 | Kurth | 538/8 |
| 2,786,832 | 3/1957 | Wender et al. | 536/8 |
| 2,950,974 | 8/1960 | Smythe | 536/8 |
| 3,429,873 | 2/1969 | Horowitz | 536/8 |
| 3,661,890 | 5/1972 | Jurd | 536/8 |
| 3,988,435 | 10/1976 | Humbert et al. | 536/8 |

OTHER PUBLICATIONS

Lutomski and Szpunar, Deutsche Apotheker—Zeitung, 112, 553–559 (1972).
Stanley and Jurd, J. Agr. Food Chem., 19, 1106–1110 (1971).

*Primary Examiner*—Johnnie R. Brown
*Assistant Examiner*—Blondel Hazel

[57] ABSTRACT

A process for the production of antimicrobial compositions from naturally occurring flavanoid glycosides. Flavanoid glycosides are acid hydrolyzed under substantially quiescent condition at a temperature within the range of about 60° C. and about 100° C. for a sufficient time to hydrolyze the flavanoid glycoside to partially hydrolyzed flavanoid compositions having antimicrobial activity.

17 Claims, No Drawings

ANTIMICROBIAL COMPOSITIONS OF MATTER AND A PROCESS FOR PREPARING ANTIMICROBIAL COMPOSITIONS OF MATTER FROM NATURALLY OCCURRING FLAVANOID GLYCOSIDES

BACKGROUND OF THE INVENTION

This invention relates to novel antimicrobial compositions of matter derived from naturally occurring flavanone glycosides and other plant phenolics. The present invention also relates to a novel process for preparing and isolating antimicrobial compositions of matter.

Over the years, many reports have appeared in the scientific literature claiming antimicrobial behavior for various natural plant phenolic compounds such as coumarin glycosides and flavanone glycosides. These various reports, however, have not been substantiated and have indeed been refuted by other workers. The antimicrobial properties of flavanoid glycosides, therefore, have remained a subject of controversy.

The broad class of chemical compounds known as flavanoid glycosides encompasses compounds including flavanone glycosides, coumarin glycosides and psoralin glycosides. Common examples of natural plant flavanoid glycosides include naringin, having the structure

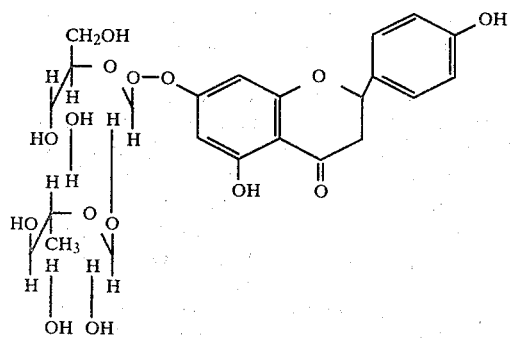

hesperidin, having the structure

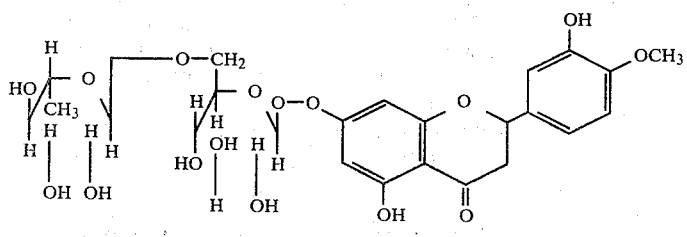

and esculin, having the structure

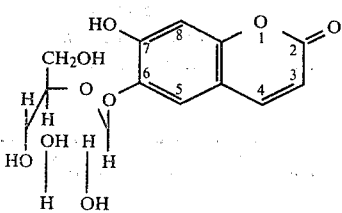

Natural plant flavanoid glycosides, which occur widely in nature, can be hydrolyzed in aqueous acid solution to yield such sugars as rhamnose and/or glucose and flavanoid aglycones. For example, hydrolysis of naringin, hesperidin, and esculin result in the formation, respectively, of the aglycones naringenin, which has the structure:

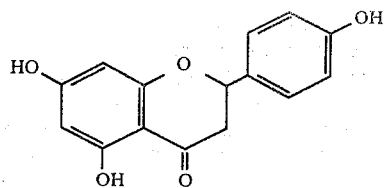

hesperetin, which has the structure:

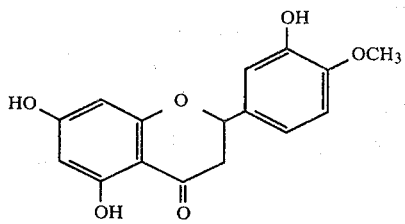

esculetin, which has the structure:

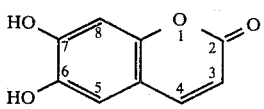

In the prior art, the common practice has been to hydrolyze flavanoid glycosides in strong acid at a pH of 1 or less for several hours, accompanied by both vigorous stirring and heating at reaction temperatures approximating 100° C. Under such conditions, the hydrolysis reaction proceeds to completion and generates flavanoid aglycones and sugars. It has been discovered, however, that if one uses dilute acid, quiescent conditions, and a limited reaction time, compositions having antimicrobial properties are obtained. In contrast, flavanoids do not possess antimicrobial properties.

The present invention permits the production of valuable antimicrobial compositions from naturally occurring plant material and clarifies the conflicting results reported in the literature with respect to the antimicrobial activity of phenolic glycosides. Specifically, the present invention teaches a process whereby one skilled in the art can easily and repeatedly convert natural flavanoid glycosides into isolable compositions of matter which have antimicrobial activity.

SUMMARY OF THE INVENTION

Antimicrobial compositions are prepared from naturally occurring flavanoid glycosides, in accordance with the present invention, by contacting a flavanoid glycoside of the formula:

X—O—Y—O—Z, wherein:
X is a flavanoid agylcone moiety,
Y is a glucose or rhamnose group, and
Z is H when Y is a rhamnose group, and H or a rhamnose group when Y is a glucose group;
with an acid which is a stronger acid than the flavanoid glycoside. The resultant hydrolysis mixture is maintained under substantially quiescent conditions at a temperature within the range of about 60° C. to about 100° C. for a sufficient time to hydrolyze the flavanoid glycoside to a product having antimicrobial activity.

The invention is also directed to antimicrobial compositions produced by the process of the present invention, disinfectant composition comprising an inert carrier and such antimicrobial compositions, and methods of controlling and destroying micro-organisms, including bacteria and fungi, by bringing such antimicrobial compositions into contact with micro-organisms.

DETAILED DESCRIPTION OF THE PREFERRED EMBODIMENTS

As is well known in the art, acid hydrolysis is a chemical reaction, catalyzed by acid, in which water reacts with another substance to form one or more new substances. As explained previously, acid hydrolysis of a flavanoid glycoside yields, as reaction products, a flavanoid aglycone and a sugar. For example, naringin can be acid hydrolyzed to yield its aglycone, naringenin, and the sugars rhamnose and glucose.

It has been discovered that isolable intermediate compounds or compositions, resulting from properly controlled acid hydrolysis of flavanoid glycosides, have excellent antimicrobial properties. These compounds or compositions, which may be termed partially hydrolyzed flavanoids, differ from both the starting flavanoid glycosides and the flavanoid aglycone reaction products.

Flavanoid glycosides useful as starting products in the method of the invention encompass such compounds as flavanone glycosides, coumarin glycosides and psoralin glycosides. Specific flavanone glycosides include naringin, hesperidin, quercetin, rutin and bio-flavanoid complexes such as the bio-flavanoid complex produced by Sunkist. Specific examples of coumarin glycosides and psoralin glycosides include, respectively, skimmin, esculin and scopoletin.

Flavanoid glycosides are generally slightly acidic in that, in a base, they donate a proton. Accordingly, for acid hydrolysis to occur in the process of the invention, the acid chosen, preferrably either a Lewis acid or a Bronsted acid, must be stronger than the particular flavanoid glycoside to be hydrolyzed. Inorganic acids, particularly mineral acide such as hydrochloric or sulfuric, may be used advantageously in the hydrolysis reation. Organic acids, such as carboxylic or oleic are also useful, but hydrochloric acid is preferred.

The relative amounts of acid and flavanoid employed in the reaction are not critical. Normally, however, sufficient acid is employed to insure more water is present than is required to theoretically completely hydrolyze the flavanoid glycoside. Because of the presence of excess water in the process of the invention, merely one extra proton is needed to catalyze the reaction. If the protons are small in number, however, the reaction will proceed at a slower rate. As the Examples will demonstrate, the inventive products begin to be formed within about fifteen minutes when an acid of 0.5 N concentration is used.

In carrying out the process of the present invention, the acid preferably has a concentration of less than 1 N and the mixture is maintained at a temperature within the range of from about 85° C. to about 98° C. for less than 3 hours. More preferably, the acid has a concentration of between about 0.3 and 0.8 N (e.g., about 0.5 N) and the mixture is maintained at a temperature within the range of from about 85° C. to about 98° C. (e.g., from about 90° C. to about 95° C.) for from about 30 minutes to about 2 hours (e.g., about 60 minutes).

In the prior art process previously referred to, the refluxing reaction mixture was typically agitated, usually by stirring. In the process of the present invention, however, acid hydrolysis is carried out under substantially quiescent conditions, with agitation being avoided.

The process of the present invention is carried out long enough to hydrolyze the flavanoid glycosides to isolable intermediate compositions matter having antimicrobial activity. If the reaction is allowed to continue too long, the isolable antimicrobial compositions will be converted to flavanoid aglycones. The specific length of time the reaction should be permitted to proceed depends, of course, on a number of factors, such as the particular reactants and particular reaction conditions, employed.

In order to avoid conversion to aglycones, it is preferred that the hydrolysis mixture be transferred to an ice water bath after completion of the desired degree of hydrolysis. The antimicrobially active intermediate compositions may be isolated, by using such well-known steps as filtering, washing and drying.

For application as a disinfectant composition, the partially hydrolyzed flavanoid compositions may be dispersed in any acceptable inert carrier, i.e., any carrier that will not react with the partially hydrolyzed compositions. Liquid carriers, such as water, ethyl alcohol, mineral oil and propylene glycol, and solid particulate materials, such talc, silica gel, clay, etc., may be used.

The following examples are designed to elucidate the teachings of the present invention, and in no way limit the scope of the invention. Various other modifications and equivalents of the examples will readily suggest themselves to those skilled in the art without departing from the spirit or scope of the present invention.

EXAMPLE 1

Eight test-tubes were prepared, each containing 1 gram of naringin (obtained from Sunkist Corporation) and 15 ml of 0.5 molar HCl. The tubes were initially placed in a hot water bath, at approximately 100° C. In order to "freeze-out" or immediately stop the reaction, the tubes were transferred at different times to an ice water bath.

| Tube Number | Time in Hot Water Bath (min.) |
|---|---|
| 1 | 30 |
| 2 | 60 |
| 3 | 90 |
| 4 | 120 |
| 5 | 150 |
| 6 | 180 |
| 7 | 220 |

| Tube Number | Time in Hot Water Bath (min.) |
|---|---|
| 8 | 240 |

Although the tube 1 solution, when removed, was clear, a gummy precipitate formed when the tube was cooled. After thirty-five minutes a precipitate began forming in all the remaining tubes. An oil, which began forming at the top of all tubes after forty minutes, moved to the bottom of each tube within five additional minutes.

At 80 minutes, all remaining solutions were clear, with the oily, active precipitate still at the bottom. At 100 minutes, the oil began to disappear and crystals began growing from the oil layer, while, at about the same time, a layer of clear, light yellow crystals began forming near the top of the solutions.

The precipitates were filtered out from tubes 1-8 and washed with about 150 ml of distilled $H_2O$ to substantially remove all remaining acid. After washing, the precipitates were vacuum dried in an oven at about 50° C. for about two hours.

In order to ascertain the antimicrobial activity of the dried samples, they were pulverized and 10.0 mg of each were weighed into small test tubes. After dissolution in 10.0 ml of spectrophotometric grade acetone, each sample was pipetted onto a separate, sterile, dry, 6 mm diameter, filter paper disc. After allowing for evaporation at about 50° C., the pipetting and drying steps were subsequently repeated until each 10.0 mg sample was completely transferred to a disc.

The discs, when dry, were each applied to the surface of 150×15 mm Trypticase Soy Agar petri-dish, previously swabbed, following the Kirby-Bauer technique, with a suspension of S. aureus ATCC 6538. Great care was taken to place the sample-containing surface of each prepared disc in contact with the bacteria. After 60 minutes at room temperature, the petri-dishes were incubated at 37° C. for 18 hours.

Inhibition zone diameters were measured four times to the nearest estimated 0.1 mm with a clean rule. The results appear in Table I.

TABLE I

| Test Tube Sample | Solvent to Dissolve | Inhibition Zones (mm) versus S. aureus ATCC 6538 (including diameter of the disc) | Inhibition Zone Mean X |
|---|---|---|---|
| 1 | Acetone | 10.0, 9.8, 10.0, 9.7 | 9.9 |
| 2 | Acetone | 12.0, 12.0, 12.0, 12.0 | 12.0 |
| 3 | Acetone | 10.0, 9.8, 9.8, 10.0 | 9.9 |
| 4 | Acetone | 9.8, 10.0, 9.5, 9.8 | 9.8 |
| 5 | Acetone | 8.5, 8.5, 8.3, 8.5 | 8.4 |
| 6 | Acetone | 8.0, 7.9, 7.8, 7.8 | 7.9 |
| 7 | Acetone | 7.0, 7.0, 6.8, 7.0 | 7.0 |
| 8 | Acetone | 7.0, 7.2, 7.0, 7.0 | 7.0 |
| blank disc | none | no zone | — |

In this example of the hydrolysis of naringin, the level of antimicrobial activity of the partial hydrolysis products varied with reaction time, reaching a maximum of about 60 minutes.

EXAMPLE 2

Nine test tubes were prepared, eight of which containing two grams of naringin (obtained from Sunkist Corporation) and 30 ml of 0.5 molar HCl. The ninth tube, a control tube, contained 2 grams of naringin and solvent, but was neither acid hydrolyzed nor heated.

Seven of the tubes (T-5, T-10, T-15, T-20, T-25, T-30, and T-360) were placed in a 75° C. water bath, which was subsequently heated to approximately 95° C. Tube T-0 was allowed to remain at room temperature for five minutes and was then placed in an ice bath. Tubes T-5, T-10, T-15, T-20, T-25 and T-30 were respectively transferred from the heated bath to an ice water bath at five minute intervals. Tube T-360 was allowed to react for six hours before cooling.

In T-0, the naringin did not appreciably dissolve in the acid. Although upon transfer, T-5 contained a clear solution, a precipitate did form several hours after transfer to the cold bath. T-10, T-15, T-20, T-25 and T-30 had small amounts of precipitate before transfer and clouded readily when placed in the ice water. T-360 containing a large amount of precipitate when removed from the hot water and formed little additional precipitate during cooling.

The precipitates from all eight tubes were filtered, washed, and vacuum dried as in Example 1. Along with the control sample of non-hydrolyzed naringin, the samples were prepared and tested for antimicrobial properties by the procedures detailed in Example 1, except that to completely dissolve the non-hydrolyzed, T-0, T-5, and T-10, samples it was necessary to use both spectrophotometric grade acetone and spectrophotometric grade methanol. The results are detailed in Table II.

TABLE II

| Sample | Solvent to Dissolve Completely | Inhibition Zone (mm) versus S. aureus ATCC 6538 (including diameter of the disc) | Inhibition Zone Mean X |
|---|---|---|---|
| blank disc | — | No zone | — |
| naringin | Acetone & MeOH | No zone | — |
| T-0 | Acetone & MeOH | No zone | — |
| T-5 | Acetone & MeOH | No zone | — |
| T-10 | Acetone & MeOH | No zone | — |
| T-15 | Acetone | 8.0, 7.8, 7.8, 7.5 | 7.8 |
| T-20 | Acetone | 8.2, 8.5, 8.2, 8.2 | 8.3 |
| T-25 | Acetone | 8.5, 8.5, 8.8, 8.8 | 8.6 |
| T-30 | Acetone | 9.2, 9.2, 9.0, 9.0 | 9.1 |
| T-360 | Acetone | 7.0, 7.0, 6.9, 6.7 | 6.9 |

EXAMPLE 3

Fourteen test tubes were prepared, each containing 2 grams naringin (obtained from Sunkist Corporation) and 30 ml of 0.5 M HCl. One tube, T-0, was left at room temperature for about thirty minutes and then placed in ice water. The remaining tubes were placed in a 99° C. hot water bath. During the reaction, the bath was maintained between 91° C. and 96° C. After thirty minutes, tube T-30 was removed and placed in an ice water bath. Thereafter a tube was transferred to the ice water bath every five minutes. The resulting precipitates were filtered, washed and vacuum dried, as in Example 1, except that during washing, the samples were spun on a vortex and the precipitates were allowed to resettle.

To monitor antimicrobial activity, the test tube samples, plus a sample of non-hydrolyzed naringin, were prepared and tested by the procedures detailed in Example 1, except that incubation lasted 16, rather than 18, hours and the samples were completely dissolved in MeOH, rather than acetone. Further, only one inhibition zone measurement was made, not four. Additionally, using means well known in the art, the pH of both the treated discs and the inhibition zones was measured. The results are tabulated in Table III.

TABLE III

| Sample | Inhibition zone (mm) versus S. aureus ATCC 6538 (including the diameter of the disc) | pH discs | pH zones |
|---|---|---|---|
| Naringin | No zone | — | — |
| T-0 | No zone | 7.0 | — |
| T-30 | 9.5 | 7.0 | 7.5 |
| T-35 | 10.5 | 7.0 | 7.5 |
| T-40 | 11.0 | 7.0 | 7.5 |
| T-45 | 9.5 | 7.5 | 8.0 |
| T-50 | 10.0 | 7.5 | 8.0 |
| T-55 | 10.0 | 7.5 | 8.0 |
| T-60 | 10.5 | 7.5 | 8.0 |
| T-65 | 11.0 | 7.5 | 8.0 |
| T-70 | 11.0 | 7.5 | 8.0 |
| T-75 | 12.0 | 7.5 | 8.0 |
| T-80 | 11.5 | 7.5 | 8.0 |
| T-85 | 12.5 | 7.5 | 8.0 |
| T-90 | 12.0 | 7.5 | 8.0 |

EXAMPLE 4

Twenty grams of crude naringin were mixed in an Erlenmeyer flask with 300 ml. of 0.5 M HCl. This mixture was heated at 90°-95° C. with no stirring for 60 minutes. The reaction mixture was cooled immediately in an ice bath and then stored in the refrigerator. The acid solution was decanted and replaced with distilled water. This step was repeated several times. The final wash water, mixed vigorously with the oily product at room temperature, gave no acid reaction to litmus paper. After decanting the final wash water, the product was taken up in 35 ml of spectrophotometric grade methyl alcohol and evaporated to dryness in a tared round bottomed flask. The yield of yellow glassy product was 11.1 g. The antimicrobial activity of this product was tested versus S. aureus as described in the previous examples. The zone of inhibition was 10.5 millimeters.

EXAMPLE 5

A crude hydrolysis product of naringin, prepared as in Example 4, was tested for antimicrobial activity against a variety of bacteria using the filter paper disc method described in Example 1. The hydrolysis product was found to inhibit the growth of B. subtillis, Micrococcus lysodeikticus, Sarcina lutea, Streptococcus faecalis, Clostridium botulinum ATCC 19397, Clostridium sporogenes, P..vulgaris ATCC 13315, Staphylococcus aureus ATCC 25923, Sepidermis ATCC 12228, S. pyogenes ATCC 19615 and S. aureus ATCC 6538.

EXAMPLE 6

In an effort to isolate the components of the hydrolysis mixture exhibiting the antimicrobial activity demonstrated in Examples 1-5, a high-pressure liquid chromatographic separation was made, using a reverse phase column and a UV absorption detector. The device may be obtained commercially from Altex Scientific Inc. 1780 Fourth St. Berkeley, Calif. 94710. The column, Altex No. 254-63, was stainless steel, 3.2×250 mm and was packed with 10 micron Lichrosorb RP-8. The eluting solvent was methanol/water, 57/43. The following operating parameters were used: 20×23 PSIG, 0.16 Au, 254 nm detector and a chart speed of 12 in/hr.

The analysis indicated two active components, F-1 with $R_f=44$ mm and F-2, with $R_f=61-63$ mm. Table IV represents relative peak size data gathered from the detector for naringin, F-1 and F-2 at reaction times of 0, 15, 30, 50, 60, 90, and 360 minutes respectively. The relative activity data was obtained as in Examples 1-3.

TABLE IV

| Reaction Time (Min) | HPLC Peak Size | | | Relative Activity |
|---|---|---|---|---|
| | Naringin Rf=41 mm | F-1 Rf=44 mm | F-2 Rf=61-63 mm | |
| 0 | only peak | | | 0 |
| 15 | moderate | moderate | small | 7.8 |
| 30 | shoulder | large | small | 9.4 |
| 50 | absent | large | small | 10.0 |
| 60 | absent | large | large | 12.0 |
| 90 | absent | small | large | 9.9 |
| 360 | absent | small | very large | 10.0 |

EXAMPLE 7

A crude hydrolysis product of naringin was produced as described in Example 4. To remove naringenin, the ultimate hydrolysis product, the crude substance was dissolved in hot water and filtered while hot. Upon cooling, the antimicrobially active hydrolysis mixture precipitated from the filtrate. The water was decanted and the gummy residue was dried in vacuuo to yield a bright yellow, glassy solid. The infrared spectrum of this substance was very similar to the infrared spectra of both naringin and naringenin. Anal. Found: C, 59.42; H, 5.38; O (by difference), 35.20; Mol. wt. (in CH$_3$OH): 358. HPLC Analysis conducted as described in Example 6, revealed the substance to be composed of 2 components.

The crude active mixture was separated by elution through a 25 cm.×2.5 cm. dia. glass column packed with LiChroprep RP-8, 25-40 micron supplied by E. Merck, Darmstadt, Germany. The eluting solvent was 57/43 CH$_3$OH/H$_2$O.

The F-1 of Example 6 was separated and isolated by evaporation of the eluting solvent as a light yellow, glassy material which melted at 148°-153° C. Anal. Found: C, 55.47; H, 5.66; O, (by difference) 38.87; average Mol. wt. (in CH$_3$OH): 456. By repeated recrystallization from water a hydrate formed which melted at 153°-157° C. Anal. Found: C, 51.87; H, 5.95; O, (by difference) 42.23. The mass spectrum and infrared spectrum of this substance where identical with the spectra of naringin. The melting point and crystalline morphology of F-1 were, however, different from those of naringin or naringenin.

The F-2 of Example 6 was separated and isolated by evaporation of the eluting solvent as a yellow-white, hexahedral crystalline material. M.P. 241°-243° C. Anal. Found: C, 64.22; H, 4.71; O, (by difference) 31.07; Average Mol. wt. (in CH$_3$OH), 296. The infrared spectrum of this material was identical with that of naringenin. The mass spectrum of this material was very similar to the mass spectrum of naringin. The melting points and crystalline morphology of F-2, however, were different from those of naringin or naringenin.

Testing demonstrates that neither F-1 nor F-2 alone exhibits substantial antimicrobial activity. In contrast, mixtures of F-1 and F-2 possess significant antimicrobial activity.

EXAMPLE 8

In a test tube, 0.5 g hesperidin was completely dissolved in 10 ml dimethyl sulfoxide (DMSO) and 0.2 ml of 0.5 m HCl. After 90 minutes in a hot water bath at approximately 90° C., the sample was transferred to an ice water bath. Although no precipitate formed, the color changed from light to dark brown during the course of treatment.

A 20 μl capacity, sterile, dry, 6 mm diameter filter paper cellulose disc was dipped into the sample and subsequently dried at 50° C. in a vacuum oven. The treated disc surface was then applied to the surface of a 150×15 mm Trypticase Soy Agar petri-dish; which had previously been swabbed by the Kirby-Bauer method with a suspension of *S. aureus* ATCC 6358. After allowing 1 hour for diffusion at room temperature, the dish was incubated at 37° C. for 18 hours. The resultant zone of inhibition against the *S. aureus* ATCC 6538, including the diameter of the disc, was found to be 9.2 mm.

EXAMPLE 9

A solution was prepared by dissolving 2 grams of hesperidin in a mixture of 0.3 grams of sodium hydroxide and 3 milliliters of water. This alkali solution was added drop wise to a refluxing solution of 1.3 ml. 35% HCl in 8.9 ml water. The addition of the alkali solution of hesperidin to the refluxing acid solution resulted in a bright yellow solution containing a white flaky precipitate.

After 30 minutes of reaction at 101° C. a brown oil formed on top of the precipitate and along the sides of the flask. After 35 minutes of reaction, the heating was stopped and the solution was immediately neutralized with 0.5 N sodium hydroxide. The neutralized solution was cooled in an ice bath and filtered. The tacky precipitate was washed with several 25 ml. portions of distilled water until the washings were free of acid.

The washed and dried precipitate was then dissolved in methyl alcohol. A twenty microliter capacity, sterile, dry, 6 mm diameter filter paper cellulose disc was dipped into the sample solution and subsequently dried at 50° C. in a vacuum oven. The treated disc surface was then applied to the surface of a 150×15 mm Trypticase Soy Agar petri-dish, which had previously been swabbed by the Kirby-Bauer method with a suspension of *S. aureus* ATCC 6358. After allowing one hour for diffusion at room temperature, the disk was incubated at 37° C. for 18 hours. The reultant zone of inhibition against the test organism was found to be 8 mm.

EXAMPLE 10

Esculin (1 gram) was placed in a test tube, mixed with 15 ml of 0.5 N HCl and heated in a water bath for 1 hour at 96° C. The test tube was then cooled in an ice bath and the precipitate was washed free of acid and dried in vacuuo. The resulting yellow crystals were tested as described in Example 1 versus *Staph. aureas* ATCC 6538. This sample, contained on a disc 13 millimeters in diameter, gave an inhibition zone of 23 millimeters.

What is claimed is:

1. A process for the production of antimicrobial compositions from naturally occurring flavanoid glycosides comprising the steps of: forming a hydrolysis mixture by contacting an acid with a flavanoid glycoside of the formula:

X—O—Y—O—Z, wherein:
X is a flavanoid aglycone moiety,
Y is a glucose or rhamnose group, and
Z is H when Y is a rhamnose group, and H or a rhamnose group when Y is a glucose group;
wherein said acid is a stronger acid than said flavanoid glycoside and further wherein said mixture is maintained under substantially quiescent conditions at a temperature within the range of about 60° C. to about 100° C. for a sufficient time to hydrolyze said flavanoid glycoside to partially hydrolyzed flavanoid compositions having antimicrobial activity, said compositions being different from either flavanoid glycosides or flavanoid aglycones.

2. The process of claim 1 wherein said acid has a concentration of less than 1 N and said mixture is maintained at a temperature within the range of from about 85° C. to about 98° C. for less than 3 hours.

3. The process of claim 2 wherein said mixture is maintained at said temperature for from about 30 minutes to less than 3 hours.

4. The process of claim 2 wherein said acid has a concentration of between about 0.3 and 0.8 N and said mixture is maintained at said temperature for from about 30 minutes to about 2 hours.

5. The process of claim 4 wherein said mixture is maintained at a temperature within the range of from about 90° C. to about 95° C. for about 60 minutes and wherein said acid has a concentration of 0.5 N.

6. The process of claim 1 wherein said mixture is transferred to an ice water bath after heating to terminate said hydrolysis reaction.

7. The process of claim 1 wherein said flavanoid glycoside is naringin.

8. The process of claim 7 wherein said mixture is maintained at said temperature for about 60 minutes.

9. The process of claim 7 further including the steps of filtering said mixture; washing said mixture with distilled water; and drying said mixture.

10. The process of claim 1 wherein the flavanoid glycoside is hesperidin.

11. The process of claim 1 wherein the flavanoid glycoside is esculin.

12. The process of claim 1 wherein said acid is selected from the group consisting of hydrochloric acid, sulfuric acid, carboxylic acid and oleic acid.

13. The process of claim 1 wherein said acid is an inorganic acid.

14. The process of claim 13 wherein said inorganic acid is hydrochloric acid.

15. A composition of matter produced by the process of any one of claims 1, 4, 5, and 7.

16. A disinfectant composition for controlling and destroying fungi and bacteria which comprises an inert carrier and an amount effective to control fungi and bacteria of the composition of matter produced by the process of any one of claims 1, 4, 5, and 7.

17. A process of controlling and destroying fungi and bacteria which comprises bringing an amount effective to control fungi and bacteria of the composition of matter produced by the process of any one of claims 1, 4, 5 and 7 into contact with said fungi or bacteria.

* * * * *

UNITED STATES PATENT AND TRADEMARK OFFICE
CERTIFICATE OF CORRECTION

PATENT NO. : 4,238,483  
DATED : December 9, 1980  
INVENTOR(S) : Stephen E. Frazier Page 1 of 3

It is certified that error appears in the above—identified patent and that said Letters Patent is hereby corrected as shown below:

Column 1, lines 27-44, change the formula to read

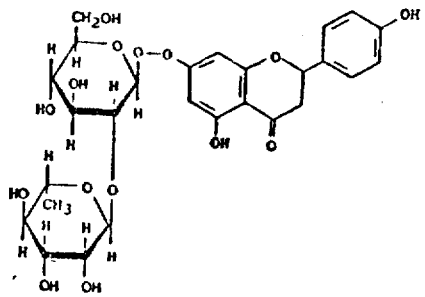

UNITED STATES PATENT AND TRADEMARK OFFICE
CERTIFICATE OF CORRECTION

PATENT NO. : 4,238,483
DATED : December 9, 1980
INVENTOR(S) : Stephen E. Frazier It is certified that error appears in the above—identified patent and that said Letters Patent is hereby corrected as shown below:

Column 1, lines 45-54, change the formula to read

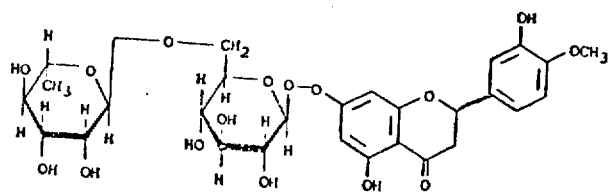

UNITED STATES PATENT AND TRADEMARK OFFICE
CERTIFICATE OF CORRECTION

PATENT NO. : 4,238,483

DATED : December 9, 1980

INVENTOR(S) : Stephen E. Frazier

It is certified that error appears in the above—identified patent and that said Letters Patent is hereby corrected as shown below:

Column 1, lines 56-65, change the formula to read

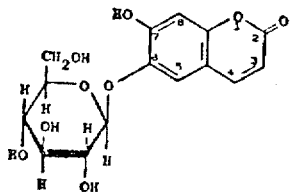

[SEAL]

Signed and Sealed this

Seventeenth Day of March 1981

Attest:

Attesting Officer

RENE D. TEGTMEYER

Acting Commissioner of Patents and Trademarks